United States Patent [19]
Winston et al.

[11] Patent Number: 6,013,072
[45] Date of Patent: Jan. 11, 2000

[54] SYSTEMS AND METHODS FOR STEERING A CATHETER THROUGH BODY TISSUE

[75] Inventors: Thomas R. Winston, Leawood; John M. Neet, Lawrence, both of Kans.

[73] Assignee: Intraluminal Therapeutics, Inc., Carlsbad, Calif.

[21] Appl. No.: 08/890,630

[22] Filed: Jul. 9, 1997

[51] Int. Cl.[7] .................................................. A61B 17/36
[52] U.S. Cl. .................................................. 606/15; 606/7
[58] Field of Search ..................... 606/8, 10, 11, 606/12, 14, 15, 16, 17, 7

[56] References Cited

U.S. PATENT DOCUMENTS

| | | | |
|---|---|---|---|
| 4,315,514 | 2/1982 | Drewes et al. | 128/653 |
| 5,041,108 | 8/1991 | Fox et al. | 606/15 |
| 5,109,859 | 5/1992 | Jenkins | 606/8 |
| 5,192,278 | 3/1993 | Hayes et al. | 606/15 |
| 5,203,779 | 4/1993 | Müller et al. | 606/15 |
| 5,540,677 | 7/1996 | Sinofsky | 606/10 |

*Primary Examiner*—Linda C. M. Dvorak
*Assistant Examiner*—Sonya C Harris
*Attorney, Agent, or Firm*—Armstrong Teasdale LLP; Scott R. Hayden; Tara A. Nealey

[57] ABSTRACT

Catheters for photoablating plaque build-up in blood vessels are described. In one form, the catheter includes a catheter body having a first group of optic fibers and a second group of optic fibers. The first group of optic fibers is adjacent the second group of optic fibers, and each group of optic fibers includes at least one optic fiber having a first end and a second end. The second ends of the respective optic fibers form a substantially rounded hemispherical catheter head. A control element is coupled to the catheter body and is configured to selectively transmit energy through either the first group of optic fibers, or the second group of optic fibers, or both the first and second groups of optic fibers.

25 Claims, 3 Drawing Sheets

6,013,072

SYSTEMS AND METHODS FOR STEERING A CATHETER THROUGH BODY TISSUE

FIELD OF THE INVENTION

This invention relates generally to medical catheters and, more particularly, to methods for steering, or guiding, medical catheters through body tissue.

BACKGROUND OF THE INVENTION

Atherosclerotic plaque is known to build up on the walls of arteries in the human body. Such plaque build up restricts circulation and often causes cardiovascular problems, especially when the build up occurs in coronary arteries. Accordingly, it is desirable to remove or otherwise reduce plaque build up.

Known catheters implement laser energy to remove plaque build up on artery walls. One known catheter includes a laser source and a catheter body. The catheter body has a first end and a second end, or head, and several optical fibers extend between the first end and the second end. The laser source is coupled to each of the optical fibers adjacent the catheter body first end and is configured to transmit laser energy simultaneously through the optical fibers.

To remove arterial plaque, for example, the catheter body is positioned in the artery so that the second end of the catheter body is adjacent a region of plaque build-up. The laser source is then energized so that laser energy travels through each of the optical fibers and substantially photoablates the plaque adjacent the second end of the catheter body. The catheter body is then advanced through the region to photoablate the plaque in such region.

While known laser catheters are generally acceptable in connection with removing plaque from a straight region of plaque build-up, such catheters are not optimal in connection with curved regions of plaque build-up. While advancing the energized laser catheter in the curved region, it is possible for the second end of the catheter body to contact the arterial wall adjacent the curve, which may result in perforation of the arterial wall.

Until now, it was believed that a guide wire must be used to facilitate steering a catheter through a curved region of plaque build-up without perforating the arterial wall. Particularly, a guide wire is advanced through the artery and region of plaque build-up so that it forms a path through the artery and plaque build-up. The catheter is then guided through the artery using the guide wire.

While guide wires facilitate steering catheters through curved regions of plaque build-up, inserting guide wires is time consuming and tedious. In addition, it often is not feasible to insert a guide wire into an artery. For example, a guide wire typically can not be inserted into a totally occluded artery, which results in subjecting a patient to bypass surgery.

Accordingly, it would be desirable to provide a catheter which may be advanced through a curved region of plaque build-up without requiring a guide wire. It also would be desirable to provide such a catheter which may be advanced through a totally occluded artery by removing plaque in such region.

SUMMARY OF THE INVENTION

These and other objects are attained by an catheter which, in one embodiment, includes a catheter body having a first group of optic fibers and a second group of optic fibers. The first group of optic fibers is adjacent the second group of optic fibers, and each group of optic fibers includes at least one optic fiber having a first end and a second end. The second ends of the optic fibers form a substantially rounded and self-centering catheter head.

A control element is communicatively coupled to the first ends of the respective optic fibers and is configured to transmit energy through the optic fibers of each respective group. Particularly, the control element is configured to selectively transmit energy through either the first group of optic fibers, or the second group of optic fibers, or both the first and second groups of optic fibers simultaneously.

The catheter is inserted into a body passage, e.g., an artery or other blood vessel, and advanced until the catheter head is adjacent a region of blockage, e.g., a region of plaque build-up. The catheter is then advanced through the region of blockage by selectively energizing one of the groups of optic fibers or both of the groups of optic fibers. Particularly, while the region of blockage is substantially straight, the catheter is advanced while the control element transmits energy through both the first and second groups of optic fibers to photoablate the blockage adjacent the catheter head. While the region of blockage is curved, for example, so that the arterial wall is adjacent the first group of optic fibers, however, the control element PATENT transmits energy solely through the second group of optic fibers. Alternatively, while the region of blockage is curved so that the arterial wall is adjacent the second group of optic fibers, the control element transmits energy only through the first group of optic fibers. Accordingly, while advancing the advancing catheter through a curved region, the catheter only photoablates blockage adjacent the respective energized group of fibers, e.g., blockage away from the arterial wall, to form a path through such blockage and the self-centering head facilitates maneuvering the head along such path.

The above-described catheter may be advanced through a curved region without requiring a guide wire. Such catheter also may be advanced through a totally occluded artery by removing plaque in the blockage region.

DETAILED DESCRIPTION

Figure 1:
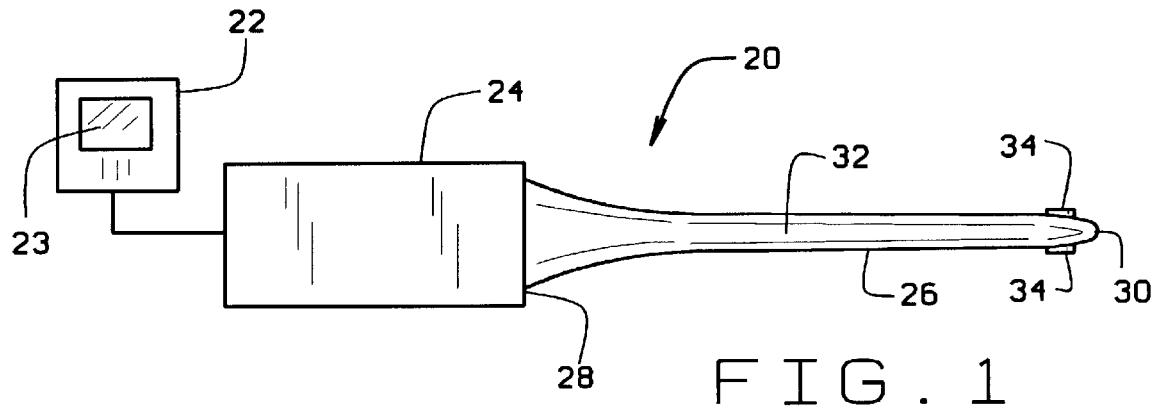
FIG. 1 is a pictorial illustration of a catheter in accordance with one embodiment of the present invention.

FIG. 1 is a pictorial illustration of a catheter 18 in accordance with one embodiment of the present invention. Catheter 18 includes a sensing system 20 having an imaging screen 22, a control element 24, and a catheter body 26. Catheter body 26 has a first, or proximate, end 28 and a rounded, or substantially hemispherical, second end, or head, 30, and includes at least two groups, or bundles, of optic fibers (not shown in FIG. 1) bundled in a housing 32. Catheter head 30 may, for example, be substantially self-centering.

Sensors, or sensing elements, 34, are coupled to catheter body 26 adjacent catheter head 30 and are configured to transmit sensing signals to sensing system 20. Sensing elements 34 may, for example, be either laser interferometry sensors or ultrasonic sensors. Alternatively, sensing elements 34 may be optic fibers extending the length of catheter body 26 configured for visual, laser interferometry, or ultrasonic conductance measurement techniqes. In addition, while sensing elements 34 are shown coupled to the exterior of housing 32, sensing elements 34 may be coupled to the interior of housing 32.

Control element 24 is communicatively coupled to first end 28 of catheter body 26, and is configured to transmit an energy beam through each group of optic fibers in catheter body 26. Particularly, control element 24 includes at least one laser source (not shown in FIG. 1) configured to emit an energy beam and at least one beam spitter (not shown in FIG. 1). The beam spitter is substantially aligned with the laser source and is positioned to split the energy beam emitted from the laser source into two substantially equal secondary energy beams so that one of the secondary energy beams is aligned with the first group of optic fibers and so that the other of the secondary energy beams is aligned with the second group of optic fibers.

Sensing system 20 is coupled to sensing elements 34 and is configured to generate an image utilizing sensing signals received from sensing elements 34. Particularly, sensing system 20 utilizes the sensing signals to display an image on imaging screen 22. Sensing system 20 may, for example, include a computer configured to receive the sensing signals, generate image data using the sensing signals, and transmit the image data for display on imaging screen 22. Obtaining sensing signals and displaying corresponding images from sensing elements 34 is well known.

Sensing system 20 also is coupled to control element 24 and configured to transmit control signals to control element 24. Particularly, sensing system 20 utilizes the sensing signals to generate control signals for selectively energizing various groups of optic fibers. For example, the sensing system computer may be configured to receive the sensing signals, generate control signals using the sensing signals, and transmit control signals to control element 24, as is described in more detail below.

Figure 2:
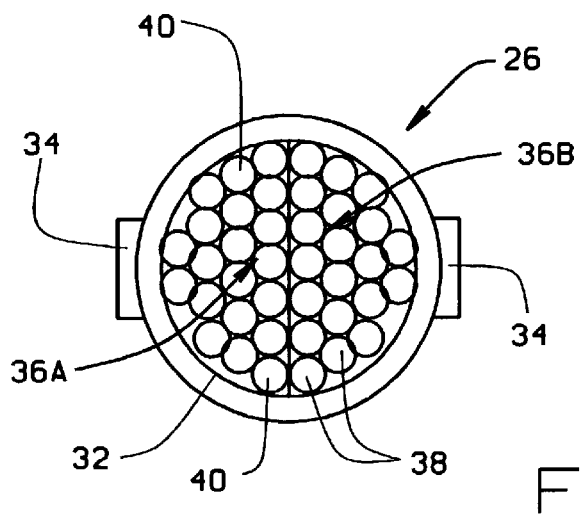
FIG. 2 is a front cross section view of the catheter body shown in FIG. 1.
Figure 1A:
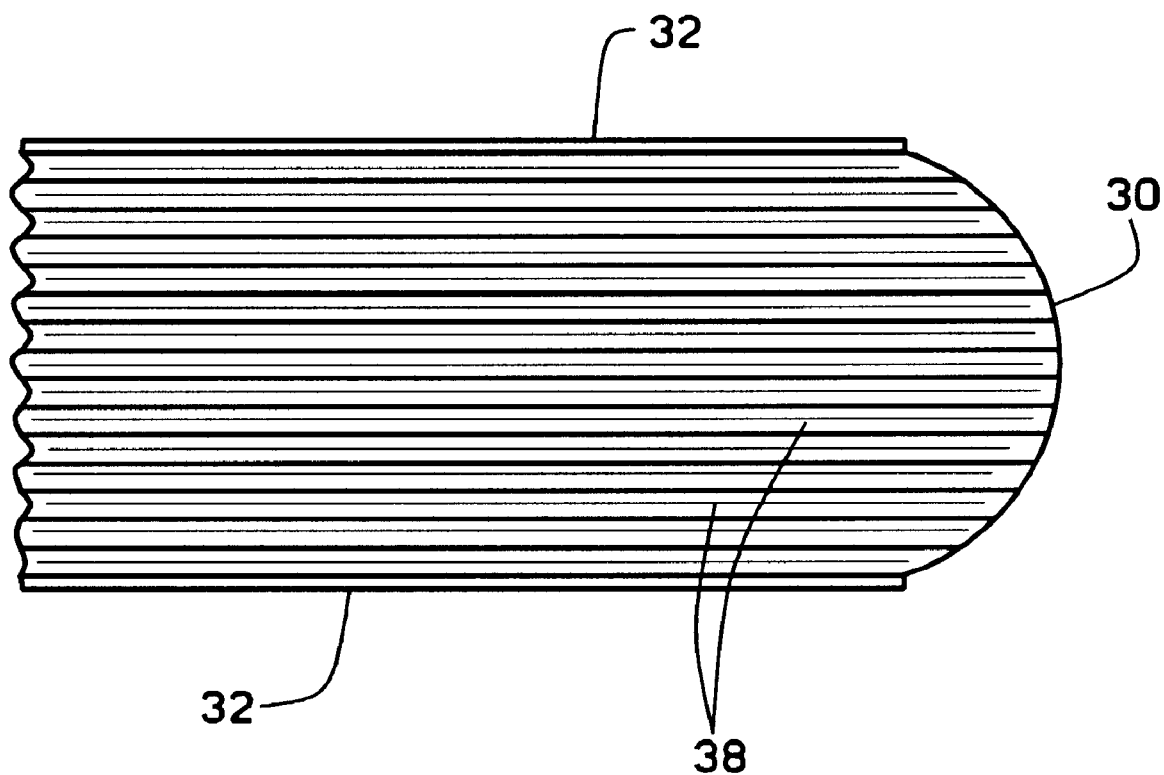
FIG. 1A is a side sectional view of a catheter head of the catheter.

Referring to FIG. 2 FIG. 1A and, catheter body 26 includes two groups, or bundles, 36A and 36B of optic fibers 38. Optic fibers 38 each include a first end (not shown in FIG. 2) and a second end 40, and second ends 40 of optic fibers 38 form catheter head 30. Particularly, second ends 40 of first group 36A of optic fibers 38 define a first region of catheter head 30 and second ends 40 of second group 36B of optic fibers 38 define a second region of catheter head 30. While first and second groups 36A and 36B, respectively, of optic fibers 38 are shown including several optic fibers 38, each group may include either fewer, e.g., one, or more optic fibers 38.

Figure 3:
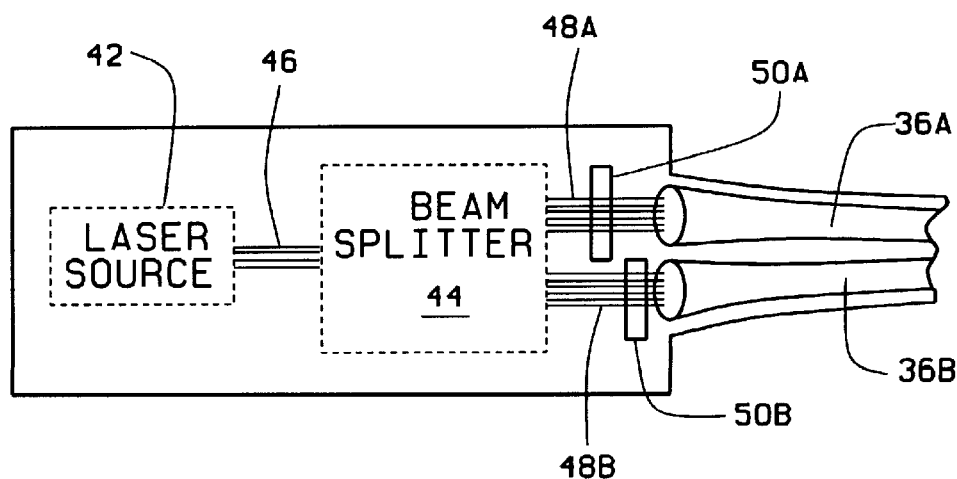
FIG. 3 is a pictorial illustration of the control element shown in FIG. 1.

As shown more clearly in FIG. 3, control element 24 includes a laser source 42 and one beam splitter 44. Beam splitter 44 is substantially aligned with laser source 42 and is positioned to split an energy beam 46 emitted from laser source 42 into two substantially equal secondary energy beams 48A and 48B so that secondary energy beam 48A is aligned with first group 36A of optic fibers 38 and so that secondary energy beam 48B is aligned with second group 36B of optic fibers 38.

Control element 24 further includes two shutters 50A and 50B. Shutter 50A is configured to move between a first position (shown in FIG. 3), where shutter 50A substantially prevents secondary energy beam 48A from being transmitted through optic fibers 38 in first fiber group 36A, and a second position (not shown in FIG. 3), where shutter 50A does not prevent secondary energy beam 48A from being transmitted through optic fibers in first fiber group 36A. Similarly, shutter 50B is configured to move between a first position (shown in FIG. 3), where shutter 50B substantially prevents secondary energy beam 48B from being transmitted through optic fibers 38 in second fiber group 36B, and a second position (not shown in FIG. 3), where shutter 50B does not prevent secondary energy beam 48B from being transmitted through optic fibers 38 in second fiber group 36B.

In addition, shutters 50A and 50B each are coupled to sensing system 20 (not shown in FIG. 3). Particularly, shutters 50A and 50B are configured to move between their respective first and second positions in accordance with the control signals transmitted by sensing system 20.

Figure 4:
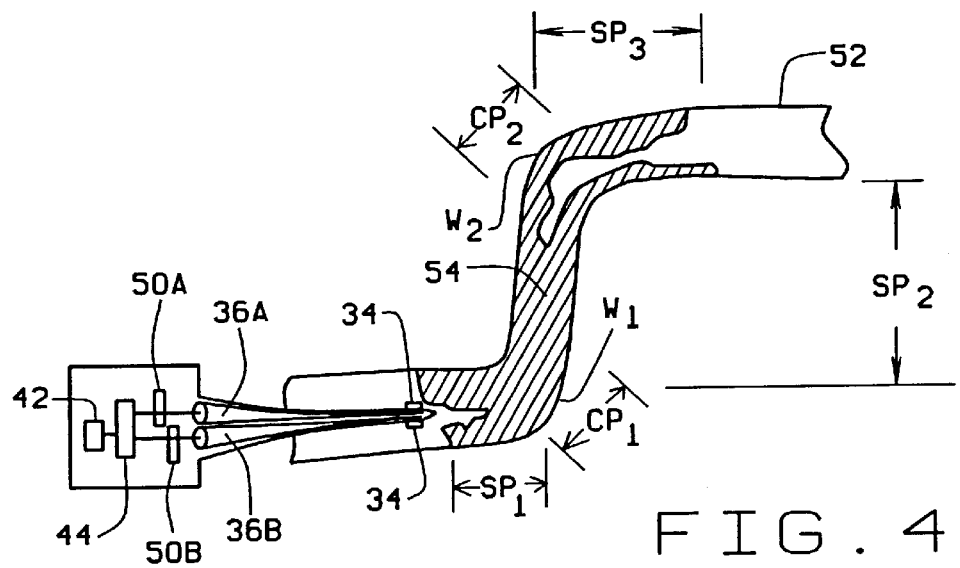
FIG. 4 is a pictorial illustration of the catheter shown in FIG. 1 inserted into a blood vessel.

Referring now to FIG. 4, to remove blockage from a blood vessel 52, e.g., an artery, catheter 26 is inserted into blood vessel 52 and advanced until catheter head 30 is adjacent a region of blockage 54, e.g., a region of plaque build-up. To remove blockage from straight portion $SP_1$ of blockage region 54, laser source 42 is activated, e.g., by sensing system 20, to transport energy beams through first and second groups 36A and 36B, respectively, of optic fibers 38 and photoablate the blockage adjacent catheter head 30. While advancing catheter head 30 through first straight portion $SP_1$ of blockage region 54, imaging screen 22 displays an image of the area adjacent catheter head in accordance with the sensing signals transmitted by sensing elements 34.

When catheter head 30 approaches a first curved portion $CP_1$ of blockage region 54, shutter 50B is positioned to block secondary energy beam 48B to avoid photoablating blood vessel 52 adjacent second group 36B of optic fibers 38. Particularly, when the sensing signals indicate that catheter head 30 is adjacent curved artery wall $W_1$, sensing system 20, e.g., the sensing system computer, transmits control signals to shutter 50B so that shutter 50B moves to block secondary energy beam 48B. Catheter head 30 is advanced through blood vessel 52 and secondary energy beam 48A continues to transmit through first group 36A of optic fibers 38 to photoablate blockage adjacent second ends 40 of such fibers 38. First group 36A of optic fibers 38 photoablates a path through blockage away from artery wall $W_1$, and self-centering catheter head 30 travels through such path, thus steering catheter head 30 through first curved portion $CP_1$ of blockage region 54.

Once catheter head 30 enters a second straight portion $SP_2$ of blockage region 54, sensing system 20 transmits control signals to shutter 50B, and shutter 50B is moved to the second position so that secondary energy beams 48A and 48B are again simultaneously transmitted through both first group 36A and second group 36B of optical fibers 38. Catheter head 30 is then advanced through second straight portion $SP_2$ until catheter head 30 approaches second curved portion $CP_2$ of blockage region 54.

Upon approaching second curved portion $CP_2$ of blockage region 54, shutter 50A is moved to the first position to block secondary energy beam 48A from transmitting through first group 36A of optic fibers 38 and to avoid photoablating blood vessel 52 adjacent first group 36A of optic fibers 38. Particularly, when sensing signals indicate that catheter head 30 is adjacent curved artery wall $W_2$, sensing system 20 transmits control signals to shutter 50A so that shutter 50A moves to block secondary energy beam 48A. Shutter 50B is simultaneously positioned in the second position to allow secondary energy beam 48B transmit through second group 36B of optic fibers 38 and photoablate blockage adjacent second ends 40 of such optic fibers 38.

Catheter head 30 is then advanced through second curved portion $CP_2$ of blockage region 54 until catheter head 30 is positioned in a third straight portion $SP_3$ of blockage region 54. Upon reaching third straight portion $SP_3$ of blockage region 54, sensing system 20 transmits control signals to shutter 50A to return to its second position, so that secondary energy beams 48A and 48B again are simultaneously transmitted through optic fibers 38. Catheter 18 is then advanced through third straight portion $SP_3$ until catheter head 30 emerges blockage region 54 and into a substantially clear region 56 or artery 52.

After advancing catheter head 30 through blockage region 54, catheter 18 may be used as a guide wire for other medical apparatus. For example, a catheter having a larger diameter than catheter 18 may be advanced through blockage region 54 utilizing catheter 18 as its guide wire.

Laser source 42 and shutters 50A and 50B may, for example, be remotely operated via sensing system 20. Alternatively, laser source 42 and shutters 50A and 50B may be operated by hand.

Catheter head 30 may be advanced, for example, manually, e.g., by hand, or automatically. Specifically, sensing system 20 may further include a motor, e.g., a stepper motor, coupled to the sensing system computer. In such case, the stepper motor also is coupled to catheter head 30 and is configured to advance catheter head 30 within the artery.

The above-described catheter 18 may be advanced through curved regions of blockage without requiring a guide wire device. Such catheter also may be advanced through a totally occluded region while simultaneously removing plaque in such region. Of course, it is to be understood that modifications may be made to catheter 18 and still be within the scope of the invention.

For example, catheter 18 includes sensing system 20 for providing automatic feed back control of fiber groups 36A and 36B, e.g., to automatically control shutters 50A and 50B. However, sensing system 30 may be used merely to display images on imaging screen 22, and an operator may selectively energize and de-energize fiber groups 36A and 36B by utilizing the displayed images.

Also, while catheter 18 was described in connection with a rounded catheter head 30, catheter head 30 may have a different shape, e.g., conical, elliptical, or spherical. Moreover, while catheter head 30 was described as self-centering, catheter head 30 may not be self-centering.

In addition, catheter 18 was described in connection with shutters 50A and 50B for blocking, or unblocking, respective secondary energy beams 48A and 48B. In an alternative embodiment, mirrors are used for blocking such secondary energy beams. Specifically, one mirror is positioned between beam splitter 44 and respective fiber groups 36A and 36B, and each mirror is configured to move between a first position, where such mirror permits its respective secondary energy beam 48A and 48B to transmit through respective fiber group 36A and 36B, and a second position, where such mirror substantially prevents its respective secondary energy beam 48A and 48B from transmitting through respective fiber group 36A and 36B. The mirrors may either be remotely operated by sensing system 20, e.g., by the sensing system computer, or manipulated by hand.

Moreover, while the catheter described above includes two groups of optic fibers, the catheter may include more than two groups of optic fibers. For example, the catheter may include three groups, four groups, five groups, six groups, seven groups, or eight groups of optic fibers. The catheter may, if desired, include more than eight groups, e.g., twelve groups, of optic fibers.

Figure 5:
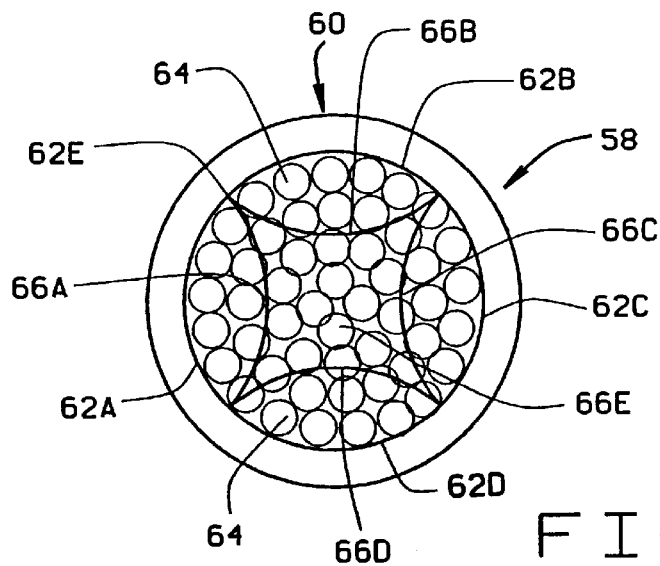
FIG. 5 is a front cross section view of a catheter body in accordance with another embodiment of the present invention.

For example, and referring now to FIG. 5, a catheter 58 in accordance with another embodiment of the present invention includes a catheter body 60 having five groups, or bundles, 62A, 62B, 62C, 62D, and 62E of optic fibers 64. Optic fibers 64 each include a first end and a second end (not shown in FIG. 5), and the second ends of optic fibers 64 form a self-centering catheter head (not shown in FIG. 5). The second ends of first group 62A of optic fibers 64 define a first region, or portion, of the catheter head, the second ends of second group 62B of optic fibers 64 define a second region, or portion, of the catheter head, the second ends of third group 62C of optic fibers 64 define a third region, or portion of the catheter head, the second ends of fourth group 62D of optic fibers 64 define a fourth region, or portion, of the catheter head, and the second ends of fifth group 62E of optic fibers 64 define a fifth region, or portion, of the catheter head.

Each group 62A, 62B, 62C, 62D, and 62E of optic fibers 64 includes one sensing optic fiber, or sensing element, 66A, 66B, 66C, 66D, and 66E, respectively. Sensing fibers 66A, 66B, 66C, 66D, and 66E are coupled to a sensing system (not shown in FIG. 5), e.g., sensing system 20, and configured to propagate ultrasound signals therethrough for generating image signals and control signals. Particularly, each sensing fiber 66A, 66B, 66C, 66D, and 66E includes a distal end (not shown in FIG. 5), and each distal end is configured to transmit and receive an ultrasound signal to tissue adjacent respective group 62A, 62B, 62C, 62D, and 62E of optic fibers 64.

Figure 6:
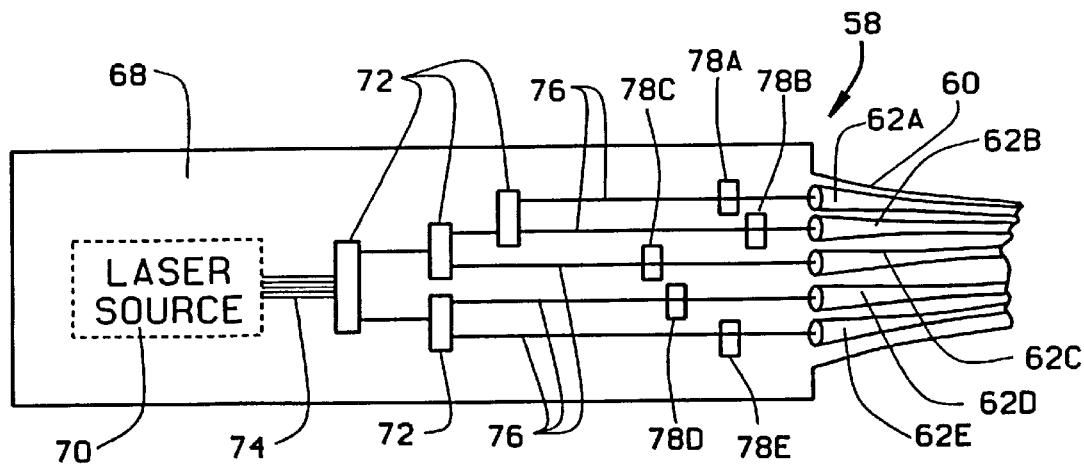
FIG. 6 is a pictorial illustration of a control element coupled to the catheter body shown in FIG. 5.

Referring to FIG. 6, a control element 68 is communicatively coupled to catheter body 60 and includes a laser source 70 and four beam splitters 72. Laser source 70 is configured to emit an energy beam 74, and beam splitters 72 are positioned to split energy beam 74 into five secondary beams 76A, 76B, 76C, 76D, and 76E, which are aligned with respective fiber groups 62A, 62B, 62C, 62D and 62E.

Control element 68 further includes five shutters 78A, 78B, 78C, 78D, and 78E, which are coupled to the sensing system. Shutter 78A is configured to move between a first position, where shutter 78A substantially prevents secondary energy beam 76A from being transmitted through optic fibers 64 in first fiber group 62A, and a second position, where shutter 78A does not prevent secondary energy beam 76A from being transmitted through optic fibers in first fiber group 62A. Similarly, shutters 78B, 78C, 78D, and 78E are configured to move between a first position, in which such shutter 78B, 78C, 78D and 78E substantially prevents respective secondary energy beam 76B, 76C, 76D and 76E from being transmitted through optic fibers 64 in respective fiber groups 62B, 62C, 62D and 62E, and a second position, where such shutter 78B, 78C, 78D and 78E does not prevent respective secondary energy beam 76B, 76C, 76D and 76E from being transmitted through optic fibers 64 in respective fiber groups 62B, 62C, 62D and 62E.

Catheter 58 is then advanced through an artery in substantially the same manner as described above with respect to catheter 18. Particularly, sensing fibers 66A, 66B, 66C, 66D, and 66E, the sensing system, and control element 68 cooperate to selectively move shutters 78A, 78B, 78C, 78D, and 78E, and to selectively energize and de-energize respective groups 62A, 62B, 62C, 62D, and 62E of optic fibers 64.

The above-described catheter 58 may be advanced through curved regions of blockage without requiring a guide wire device. Such catheter also may be advanced through a totally occluded region while simultaneously removing plaque in such region.

While the above-described catheters were described in connection with laser energy, it is to be understood that such catheters may be utilized in connection with other types of energy. For example, ultrasound or thermal energy may transmitted through the groups of optic fibers to cavitate or otherwise bore through arterial plaque.

In addition, while such catheters are described in connection with an artery, such catheters may be inserted and steered through other body passages. Moreover, such catheters may be utilized to create a passage in body tissue. For example, such catheters may be inserted and steered through a liver to create a path to a tumor in the liver. The catheters may then photoablate the tumor, or another medical instrument may be extended through the path to remove the tumor.

From the preceding description of the present invention, it is evident that the objects of the invention are attained. Although the invention has been described and illustrated in detail, it is to be clearly understood that the same is intended by way of illustration and example only and is not be taken by way of limitation. For example, while each group of optic fibers described above included more than one optic fiber, at least one group of optic fibers may include only one optic fiber. In addition, while the sensing elements were described above as ultrasound sensors, such elements may be optic fibers configured to apply laser interferometry. Further, while the catheter head described herein was hemispherical, the catheter head may have a different shape, e.g., conical. Accordingly, the spirit and scope of the invention are to be limited only by the terms of the claims.

What is claimed is:

1. A catheter comprising:
   a catheter body comprising at least two groups of optic fibers, each group of optic fibers comprising at least one optic fiber having a first end and a second end, said optic fiber second ends forming a substantially hemispherical catheter head; and
   a control element communicatively coupled to said catheter body, said control element configured to transmit energy through said at least one optic fiber of one of said optic fiber groups without simultaneously transmitting energy through said at least one optic fiber of another of said optic fiber groups, said catheter head configured to ablate a tissue adjacent said second end of said at least one optic fiber through which energy is transmitted.

2. A catheter in accordance with claim 1 wherein said catheter body comprises between three and eight optic fiber groups, and wherein said control element is further configured to transmit energy through said at least one optic fiber of at least one of said optic fiber groups without simultaneously transmitting energy through said at least one optic fiber of another of said optic fiber groups.

3. A catheter in accordance with claim 1 further configured to transmit energy substantially simultaneously through said at least one optic fiber of each of said optic fiber groups.

4. A catheter in accordance with claim 1 wherein at least one of said optic fiber groups comprises a sensing fiber.

5. A catheter in accordance with claim 1 wherein said control element comprises a laser source and at least one beam splitter, said beam splitter configured to split an energy beam emitted from said laser source into two substantially equal energy beams, said beam splitter substantially aligned with said laser source and positioned so that a first of said two substantially equal energy beams is substantially aligned with said at least one fiber of one of said optic fiber groups and so that a second of said two substantially equal energy beams is substantially aligned with said at least one fiber of another of said fiber group groups.

6. A catheter in accordance with claim 5 wherein said control element further comprises at least one shutter, said shutter configured to move between a first position, where said shutter substantially prevents said first substantially equal energy beam from being transmitted through said at least one fiber of said one of said optic fiber groups, and a second position, where said shutter does not prevent said first substantially equal energy beam from being transmitted through said at least one fiber of said one of said optic fiber groups.

7. A catheter in accordance with claim 6 further comprising a second shutter, said second shutter configured to move between a first position, where said shutter substantially prevents said second substantially equal energy beam from being transmitted through said at least one fiber of said another of said optic fiber groups, and a second position, where said shutter does not prevent said second substantially equal energy beam from being transmitted through said at least one fiber of said another of said optic fiber groups.

8. A catheter in accordance with claim 5 wherein said control element further comprises at least one mirror, said mirror configured to move between a first position, where said mirror substantially prevents said first substantially equal energy beam from being transmitted through said at least one fiber of one of said optic fiber groups, and a second position, where said mirror does not prevent said first substantially equal energy beam from being transmitted through said at least one fiber of said one of said optic fiber groups.

9. A catheter in accordance with claim 8 further comprising a second mirror, said second mirror configured to move between a first position, where said mirror substantially prevents said second substantially equal energy beam from being transmitted through said at least one fiber of said another of said optic fiber groups, and a second position, where said mirror does not prevent said second substantially equal energy beam from being transmitted through said at least one fiber of said another of said optic fiber groups.

10. A catheter in accordance with claim 1 wherein said catheter body further comprises a substantially hemispherical catheter head.

11. A catheter in accordance with claim 1 wherein said catheter body further comprises a substantially spherical catheter head.

12. A catheter in accordance with claim 1 wherein said catheter body further comprises a substantially conical catheter head.

13. A catheter in accordance with claim 1 further comprising at least one sensing element.

14. A method for steering a medical apparatus through body tissue, the apparatus including a catheter body comprising at least two groups of optic fibers, each group of optic fibers comprising at least one optic fiber having a first end and a second end, the optic fiber second ends forming a substantially hemispherical catheter head, said method comprising the steps of:

positioning the substantially hemispherical catheter head adjacent the body tissue so that the second end of the at least one optic fiber of at least one group of optic fibers is adjacent the body tissue; and selectively energizing the at least one group of optic fibers.

15. A method in accordance with claim 14 wherein the body tissue is an occlusion in a blood vessel, and wherein positioning the head adjacent the body tissue comprises the step of inserting the head in the blood vessel.

16. A method in accordance with claim 14 wherein the medical apparatus is a catheter having at least two groups of optic fibers, each group of optic fibers having at least one optic fiber, wherein a laser source is communicatively coupled to the groups of optic fibers, the laser source configured to transmit an energy beam through each group of optic fibers, and wherein said method comprises the step of:

transmitting an energy beam through at least one of the groups of optic fibers without simultaneously transmitting an energy beam through at least one of the other of the groups of optic fibers.

17. A method in accordance with claim 16 further comprising the step of transmitting an energy beam through at least two of the groups of optic fibers.

18. A method in accordance with claim 15 further comprising the step of generating an image of the blood vessel.

19. A method in accordance with claim 18 wherein the image is generated utilizing laser interferometry.

20. A method in accordance with claim 18 wherein the image is generated utilizing ultrasound.

21. A method in accordance with claim 16 wherein the catheter further includes a sensing system configured to generate sensing signals, and wherein said method further comprises the steps of:

determining appropriate head portions to energize utilizing the sensing signals; and energizing the appropriate head portions.

22. A medical system comprising:

a catheter comprising a catheter body, said catheter body comprising at least two groups of optic fibers, each group of optic fibers comprising at least one optic fiber having a first and a second end, said optic fiber second ends forming a substantially hemispherical catheter head, said substantially hemispherical catheter head having at least two portions, each portion corresponding to one of said at least two groups of optic fibers; and a control element communicatively coupled to said catheter, said control element configured to transmit energy through said catheter to a body tissue adjacent at least one portion of said substantially hemispherical catheter head so that at least one of said at least two catheter head portions is energized at the same time as at least one other of said at least two portions of said catheter head is not energized.

23. A medical system in accordance with claim 22 further comprising:

at least one imaging element coupled to said catheter head, said imaging element configured to transmit an image signal;

a sensing system coupled to said at least one imaging element and configured to generate a control signal utilizing said image signal and to transmit said control signal to said control element for selectively energizing said catheter head portions.

24. A medical system in accordance with claim 22 wherein said control system is configured to transmit laser energy through said catheter.

25. A catheter in accordance with claim 1 wherein said catheter head is substantially self-centering.

* * * * *